US010636523B2

(12) United States Patent
Stocker

(10) Patent No.: US 10,636,523 B2
(45) Date of Patent: Apr. 28, 2020

(54) DEVICE, SYSTEM AND METHOD FOR VISUALIZATION OF PATIENT-RELATED DATA

(71) Applicant: KONINKLIJKE PHILIPS N.V., Eindhoven (NL)

(72) Inventor: Philipp Stocker, Leonberg (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 622 days.

(21) Appl. No.: 15/160,329

(22) Filed: May 20, 2016

(65) Prior Publication Data
US 2016/0350488 A1 Dec. 1, 2016

(30) Foreign Application Priority Data

May 26, 2015 (EP) .................................... 15169147

(51) Int. Cl.
*G16H 40/63* (2018.01)
*G16H 10/60* (2018.01)
(Continued)

(52) U.S. Cl.
CPC ............. *G16H 40/63* (2018.01); *A61B 5/742* (2013.01); *A61B 5/746* (2013.01); *G16H 10/60* (2018.01); *G16H 50/20* (2018.01)

(58) Field of Classification Search
CPC ........ G16H 40/63; G16H 50/20; G16H 10/60; G06F 19/00; G06F 17/246; G06F 3/00; G06F 3/048; A61B 5/742; A61B 5/746
See application file for complete search history.

(56) References Cited

U.S. PATENT DOCUMENTS

| 8,392,419 B2 * | 3/2013 | Heaton | G06F 19/00 707/737 |
| 2009/0054743 A1 * | 2/2009 | Stewart | G16H 15/00 600/301 |

(Continued)

FOREIGN PATENT DOCUMENTS

| EP | 2730217 | 5/2014 |
| EP | 2777493 | 9/2014 |

(Continued)

OTHER PUBLICATIONS

Proceedings of the 2014 Workshop on Visual Analytics in Healthcare, Nov. 15, 2014.

(Continued)

*Primary Examiner* — Christopher L Gilligan

(57) ABSTRACT

The present invention relates to device, system and method for visualization of patient-related data. To enable a user, such as a caregiver, to quickly and easily recognize if the patient's health conditions has become critical, the propose device comprises a processor for processing the obtained patient-related data for visualization. The processor is configured to generate time-dependent plots of at least two different patient-related parameters over time derived from the obtained patient-related data. Said plots are generated for common visualization in a common timing diagram on a display, wherein the scale, baseline, position and range of the plots are selected to visualize the plots in the common timing diagram without overlap at times, at which the parameter values of the respective parameters visualized by the plots are considered uncritical for the patient's health condition, and to visualize a plot with overlap with another plot at times, at which the parameter values of the parameter of said plot are considered critical for the patient's health condition.

20 Claims, 10 Drawing Sheets

(51) Int. Cl.
*G16H 50/20* (2018.01)
*A61B 5/00* (2006.01)

(56) References Cited

U.S. PATENT DOCUMENTS

| | | | |
|---|---|---|---|
| 2010/0069725 A1* | 3/2010 | Al-Ali | A61B 5/0205 |
| | | | 600/301 |
| 2011/0071414 A1 | 3/2011 | Heil | |
| 2013/0179191 A1 | 7/2013 | Bal | |
| 2015/0018651 A1 | 1/2015 | Benni | |
| 2015/0213211 A1* | 7/2015 | Zaleski | G16H 10/60 |
| | | | 715/753 |
| 2016/0012621 A1* | 1/2016 | Kanada | G06F 3/048 |
| | | | 345/440 |

FOREIGN PATENT DOCUMENTS

| | | |
|---|---|---|
| WO | 02/41137 | 5/2002 |
| WO | 2014/072900 | 5/2014 |

OTHER PUBLICATIONS

Lee, et al., "Research-oriented Clinical Data Visualization based on the Analytic Health Repository: A Case of Intermountain Healthcare", 2013.

Rind, et al., "Interactive Information Visualization to Explore and Query Electronic Health Records", Foundations and Trends in Human-Computer Interaction, vol. 5, No. 3 (2011) 207-298, 2013.

* cited by examiner

DEVICE, SYSTEM AND METHOD FOR VISUALIZATION OF PATIENT-RELATED DATA

CROSS REFERENCE TO RELATED APPLICATION

This application claims the benefit of European Patent Application Number 15169147.4 filed May 26, 2015. This application is hereby incorporated by reference herein.

FIELD OF THE INVENTION

The present invention relates to a device, system and method for visualization of patient-related data. Further, the present invention relates to a patient monitor.

BACKGROUND OF THE INVENTION

Patient monitors are widely used in healthcare, e.g. in ICUs or generally in hospitals, to monitor and visualize patient-related data, in particular clinical data such as vital signs, scores and other information related to the patient's condition. For instance, the well-known Philips IntelliVue patient monitors provide a clear view of patient information and use highly configurable screens and clinical decision support tools that reflect clinical thought processes. IntelliVue monitors collect, combine, and cross-reference physiologic data to provide a coherent picture of patient status. There are different versions of these IntelliVue monitors including portable devices, stationary standalone devices (such as bedside monitors) or PC or workstation solutions running on a conventional computer.

The large amount of available patient-related data for a single patient provides many benefits, but poses also challenge, in particular for clinicians and physicians (or, generally, any caregivers or users) trying to make sense of the patient's condition and understand the patient's medical history. Visualization and visual analytics can help to analyze, filter and illustrate this large amount of patient-related data, particularly with diagnosis and decision support for caregivers. However, visualizations should be carefully designed to be helpful and achieve such goals.

Document EP 2 730 217 A1 discloses a biological information displaying apparatus that includes a displaying section on which a measurement display screen displaying biological information under measurement, an abnormality display screen displaying information alarming an abnormality of the biological information, and the biological information at a timing when the abnormality occurs, are displayed. The biological information displaying apparatus further includes a display controlling section which is configured to display the abnormality display screen on the measurement display screen, so that the abnormality display screen is superimposed on the measurement display screen. In case where the abnormality display screen is displayed on the displaying section, the display controlling section controls the displaying section so that, even when the abnormality resolves, the information alarming the abnormality of the biological information and the biological information at the timing when the abnormality occurs are continued to be displayed on the abnormality display screen.

SUMMARY OF THE INVENTION

It is an object of the present invention to provide a device, system and method for visualization of patient-related data which further support caregivers or other users in understanding and using patient-related data, particularly in diagnosis and decision support. It is a further object to provide a corresponding patient monitor.

These objects are solved by the invention as defined by the independent claims. Advantageous embodiments are defined in the dependent claims.

In a first aspect of the present invention a device for visualization of patient-related data is presented comprising:
   a data input for obtaining patient-related data of a patient over time,
   a processor for processing the obtained patient-related data for visualization, wherein the processor is configured to generate time-dependent plots of at least two different patient-related parameters over time derived from the obtained patient-related data, said plots being generated for common visualization in a common timing diagram having a common time axis on a display, and
   a data output for outputting the generated time-dependent plots for visualization on a display,
wherein the scale, baseline, position and range of the plots are selected to visualize the plots in the common timing diagram without overlap at times, at which the parameter values of the respective parameters visualized by the plots are considered uncritical for the patient's health condition, and to visualize a given plot of said plots with overlap with another plot of said plots visualized in the common timing diagram at times, at which the parameter values of the parameter of said given plot are considered critical for the patient's health condition.

In a further aspect of the present invention a patient monitor is presented comprising a device according to the present invention and a display for visualization of the time-dependent plots generated by said device.

In a further aspect of the present invention a system is presented comprising a plurality of sensors for acquiring patient-related data and a patient monitor according to the present invention for obtaining and processing the acquired patient-related data.

In still a further aspect of the present invention a method for visualization of patient-related data is presented.

In yet further aspects of the present invention, there are provided a computer program which comprises program code means for causing a computer to perform the steps of the method disclosed herein when said computer program is carried out on a computer as well as a non-transitory computer-readable recording medium that stores therein a computer program product, which, when executed by a processor, causes the method disclosed herein to be performed.

Preferred embodiments of the invention are defined in the dependent claims. It shall be understood that the claimed method, system, patient monitor, computer program and medium have similar and/or identical preferred embodiments as the claimed device and as defined in the dependent claims.

The present invention is based on the idea to process and visualize the obtained patient-related data in way that directly and immediately allows a user to recognize if the patient is or is going to be in a (potentially) critical health condition or not. For this purpose time-dependent plots are generated from patient-related parameters over time. Said patient related parameters are generally derived from the obtained patient-related data and may be the patient-related data itself, such as a measured vital sign (e.g. heart rate, respiration rate, blood pressure, SpO2, body temperature, ECG signal, etc.). Said patient-related parameters may be one or more parameters calculated from one or more pieces of obtained patient-related data (e.g. one or more vital signs) and/or any stored or inputted patient-related data (such as medical data of the patient history, patient data (size, weight, BMI, gender, etc.), such calculated parameters being e.g. a score (e.g. the EWS (early warning score) or a risk score), a PWV (pulse wave velocity), alarms, notifications, movements, or worklist items.

Two or more plots of different patient-related parameters are hereby generated for being commonly visualized in a common timing diagram on a display. In other words, while conventionally each plot is visualized in its own diagram, the plots shall be displayed in the same diagram. However, while conventionally the plots would be crossing each other multiple times leading to a loss of clear and immediate understandability, the scale, baseline, position and range of the plots are selected according to the present invention in a particular way. This makes sure that the plots are visualized in the common timing diagram without overlap at times, at which the parameter values of the respective parameters visualized by the plots are considered uncritical for the patient's health condition, i.e. for a normal health condition the plots do not cross each other. However, at times, at which the parameter values of the parameter of a plot are considered critical for the patient's health condition, the corresponding plot is visualized with overlap with another plot, preferably with the neighboring plot.

In the context of the present invention, a common timing diagram preferably refers to a graphical representation in which two or more time-dependent plots are jointly visualized with respect to a common time axis. That is, for each point along the common time axis, the different plots visualized on the common timing diagram provide the values of corresponding patient-related parameters at a same moment in time.

In this way, it can be easily and quickly recognized by a user, namely by identifying if there are any overlaps between plots, if there is a potentially critical situation for the patient's health, which may require immediate attention of the caregiver. Such overlaps can even be recognized without intensive study of the various kinds of information, generally including several plots of various patient-related parameters, that is usually displayed on the screen, e.g. of a patient monitor, but even with only a quick look from a distance such overlaps can be recognized so that the user can easily know if there is a critical situation of the patient or not.

In this context, an overlap shall be understood as a crossing between two plots as well as a change of the sequence in which the plots are usually (for a non-critical situation) are visualized (e.g. from top to bottom or from left to right in the diagram. For instance, if two plots (e.g. for heart rate (HR) and respiration rate (RR)) are visualized on top of each other (e.g. the HR plot is visualized below the RR plot), a crossing of the two plots as well as a change in the arrangement of the plots (e.g. if the RR plot at a certain point in time crosses the HR plot and is now below the HR plot, because the RR drops to a very low (i.e. critical) value) indicates that the patient's health situation has deteriorated to a potentially critical state requiring immediate attention. This can be quickly and easily recognized by a caregiver, e.g. a nurse entering the patient's hospital room, so that he/she can immediately check if the patient is indeed in a critical state or if anything else has caused the change in the visualization of the plots, e.g. a misplacement of the RR sensor or if the patient has removed the RR sensor.

Further, in this context a critical health situation (or health condition) shall be understood as a health situation (or condition) which deteriorates to such an extent that immediate attention of a caregiver may be required to avoid a serious damage or even death of the patient. The parameter values considered as critical may be predetermined for each particular patient-related parameter, in a general sense valid for all kinds of patients and general health states. In a further refinement the parameter values considered as critical may be adapted to the patient or patient groups and/or general health states or kind of health states, and also the patient history may be taken into account.

It shall be noted that a critical health condition may not only be given if there is an overlap between two plots. There may also be a (given or upcoming) critical health condition that does not lead to an overlap of two plots. Hence, there may be other indicators used in addition to an overlap that indicate a potential critical health condition. For instance, the color, line thickness or icons used for visualization of a plot may change if the respective parameter values become critical, or the plot may start blinking, or an additional sign (e.g. an exclamation mark) may be shown in addition to the plot where it starts to become critical.

According to a preferred embodiment the processor is configured to use general default values for the scale, baseline, position and range of the plots. These general default values may be predetermined and stored in the device for default use. The default values are determined such that for a majority of patients and health situations the plots show the desired behavior.

However, there are patients and health situations where such general default values are not optimal. Hence, in another the processor is configured to use patient-related default values for selecting the scale, baseline, position and range of the plots, said patient-related default values being selected based on one or more of age, size, weight, body mass index, gender, health status, current treatment, current medication, state of consciousness, patient category of the patient. This further ensures the desired behavior of the plots, even for more unusual types of patients and health situations. The required data of the patient used for selecting the correct patient-related default values may already be stored, e.g. in the device, the patient monitor or a hospital information system to which the device is preferably connected, or may be entered or selected, e.g. via a user interface or by use of a patient identifier (e.g. a barcode or RFID assigned to the patient).

In another embodiment the processor is configured to determine the scale, baseline, position and range of the plots individually for the patient based on one or more of age, size, weight, body mass index, gender, health status, current treatment, current medication, state of consciousness, patient category of the patient. This even further improves the desired behavior of the plots. For instance, by use of an algorithm or a model, the scale, baseline, position and range of the plots may be determined based on one or more of the pieces of data about the patient. Even further, the types of patient-related parameters for which the plots shall be visualized in a common diagram, are generally considered in such a calculation.

Generally, the uppermost plot in a timing diagram (if the time axis is a horizontal axis) does not have an upper neighboring plot, and the lowermost plot does not have a lower neighboring plot. Hence, to enable recognizing critical situations the processor may further be configured to select the scale, baseline, position and range of the plots to be visualized in the common timing diagram as uppermost and lowermost plots such that the uppermost plot overlaps with an upper threshold indicator at times, at which the parameter values of the parameter of the uppermost plot increase to be considered critical for the patient's health condition, and the lowermost plot overlaps with a lower threshold indicator at times, at which the parameter values of the parameter of the lowermost plot decrease to be considered critical for the patient's health condition.

In such an embodiment it is further preferred that the processor is configured to generate an overlap indicator at the overlap of the uppermost plot with the upper threshold indicator and at the overlap of the lowermost plot with the lower threshold indicator. This further improves the user's ability to recognize if there is a potentially critical health condition. Such an overlap indicator may generally be any clearly recognizable mark, such as an arrow, circle, rectangle, line, indication in a different color or font, etc.

In another improvement of this embodiment the processor is configured to generate the overlap indicator in a way that it indicates to which extent the uppermost plot overlaps with the upper threshold indicator or the lowermost plot overlaps with the lower threshold indicator. This allows an easy recognition to which extent the health condition of the patient is deteriorated. For instance, the line thickness or angle of inclination may be used as an indicator for the extent of overlap, i.e. how thicker the line and/or how steeper the line is the larger is the extent of overlap and the stronger the patient's health condition is deteriorated.

Should the timing diagram be arranged such that the time axis is a vertical axis, the same embodiments can be applied, wherein "uppermost" and "lowermost" are replaced by "rightmost" and "leftmost" and wherein "upper" and "lower" are replaced by "right" and "left".

According to another embodiment the processor is configured to select the scale, baseline, position and range of the plots dependent on the display type and/or size. The diagram may generally be displayed on many different kinds of displays, e.g. of a PC, laptop, tablet, patient monitor, smartphone, etc. Many different types and sizes of displays are generally usable. To optimize the visualization it is adapted according to the display type and/or size.

The proposed patient monitor preferably comprises a user interface allowing a user to select and/or modify the scale, baseline, position, range and/or kind of visualization of the plots. Such a user interface may e.g. be a graphical user interface, such as a touchscreen, keypad or computer mouse. It generally allows adapting the automatically generated settings of the visualization to the actual patient and his health condition. Generally, all settings may be subject to user selection and/or modification.

The proposed patient monitor may further comprise a user interface allowing a user to select a point of a plot or a complete plot, wherein said display is configured to display the parameter value of the parameter at the selected point of said plot or of all parameters at the moment in time of the selected point or the parameter values of the parameter of the complete selected plot. Generally, the parameter values of the plots are stored, which enables a visualization of parameters values indicated by the user, e.g. by pointing to a particular point on a plot. Particularly in case of a critical health situation the explicit parameter value may be useful for the clinician to decide if there is really a critical situation or how critical the situation is.

The proposed patient monitor may further comprise a user interface allowing a user to hide one or more plots by selecting a plot that shall not be hidden or by selecting plots that shall be hidden. This may further help to recognize important information.

BRIEF DESCRIPTION OF THE DRAWINGS

These and other aspects of the invention will be apparent from and elucidated with reference to the embodiment(s) described hereinafter. In the following drawings

DETAILED DESCRIPTION OF THE INVENTION

Figure 1:
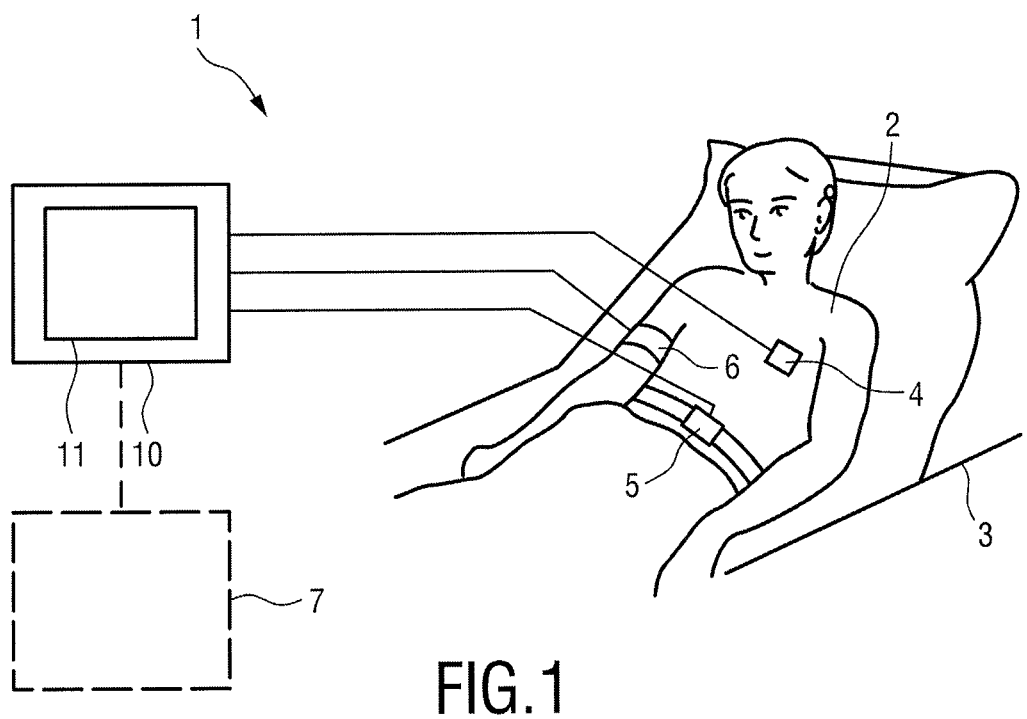
FIG. 1 shows a schematic diagram of a system according to the present invention for patient monitoring including a patient monitor according to the present invention.

FIG. 1 shows a schematic diagram of a system 1 according to the present invention for patient monitoring including a patient monitor 10 according to the present invention. The patient 2 is, in this example, lying in a bed 3, e.g. in a hospital or other healthcare facility, but may also be a neonate or premature infant, e.g. lying in an incubator, or person at home or in a different environment. Besides the patient monitor 10 the system 1 comprises a plurality of sensors for acquiring patient-related data, such as a heart rate sensor 4 for measuring the patient's heart rate, a respiration rate sensor 5 for measuring the patient's respiration rate, a blood pressure sensor 6 for measuring the patient's blood pressure, etc. Less or more sensors may be provided, particularly for measuring vital signs of the patient 2, such as an SpO2 sensor, a temperature sensor, ECG electrodes, etc. Generally, any kind of sensors for measuring a vital sign or any other patient-related data that may be of use in the desired monitoring of the patient 2 or that is desired to be used by the caregiver may generally be used in the system 1. Further patient-related data may be provided to the patient monitor from another source 7, e.g. from a laboratory, a patient history file, a hospital information system, etc.

Patient monitors are generally known in the art, such as the IntelliVue patient monitor of the applicant, which is widely used and which is available in different embodiments. Such a patient monitor generally processes the signals acquired by the sensors and visualizes them on a display 11. Hereby, not only one or more of the acquired signals may be displayed but also other patient-related data, such as scores or other data about the patient's health condition may be displayed.

Figure 2:
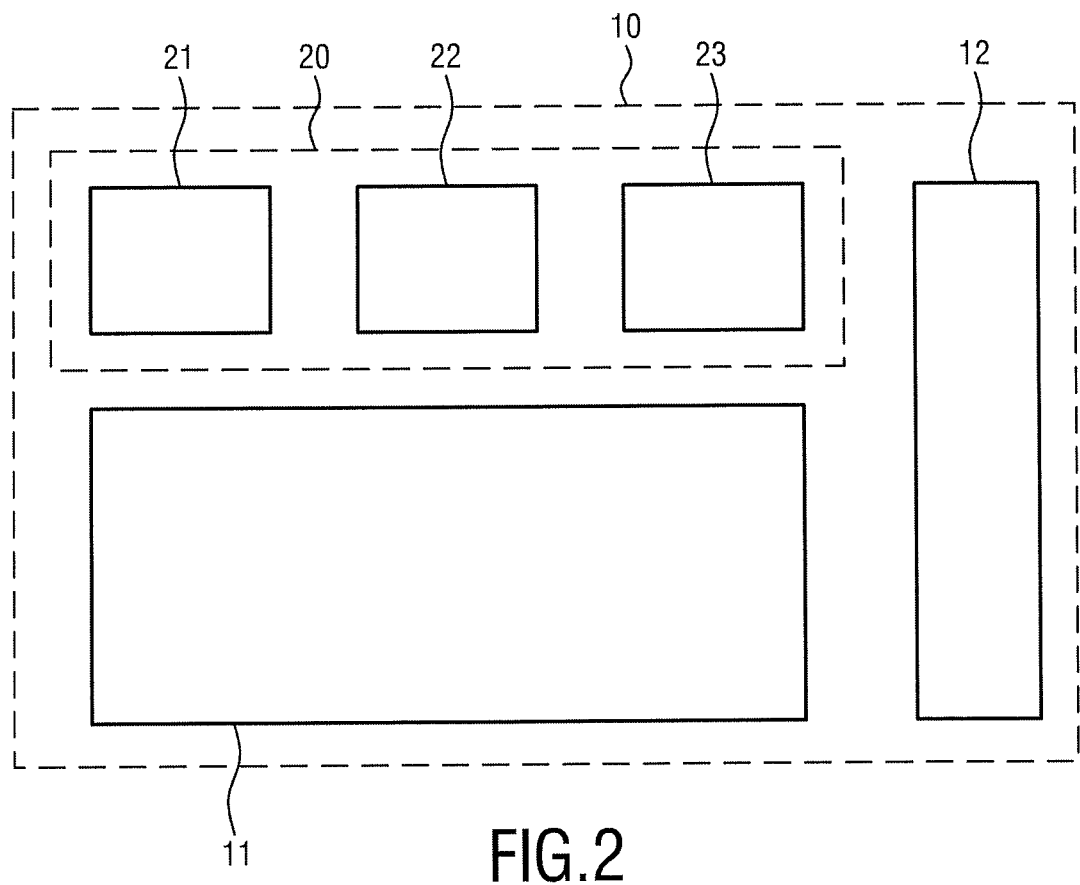
FIG. 2 shows a schematic diagram of a patient monitor according to the present invention including a device for visualization of patient-related data according to the present invention.

FIG. 2 shows a schematic diagram of a patient monitor 10 according to the present invention including a device 20 for visualization of patient-related data according to the present invention and a display 11 for visualization of the time-dependent plots generated by said device 20.

The device 20, which may e.g. be implemented by a computer or processor, comprises a data input 21, such as a data input interface coupled between the sensors 4, 5, 6 and the processor 22. The patient-related data are preferably the signals acquired by the sensors 4, 5, 6, but may also (partly or completely) be data stored in a storage (e.g. of a hospital archive) for processing by the device 20.

The device 20 further comprises a processor 22 for processing the obtained patient-related data for visualization. Hereby, time-dependent plots of at least two different patient-related parameters over time derived from the obtained patient-related data are generated. The patient-related parameters may correspond to the patient-related data, i.e. may e.g. be a measured vital sign such as the heart rate, respiration rate or blood pressure, and/or may be parameters derived from measured data, such as a health score or risk score or another physiological parameter or information related to the patient's health condition.

Generally, the time-dependent plots are separately depicted in separate timing diagrams, e.g. on top of each other and in separate windows on the display. According to the present invention, in contrast, the time-dependent plots are generated for common visualization in a common timing diagram on the display 11. Particularly the scale, baseline, position and range of the plots are selected to visualize the plots in the common timing diagram without overlap at times, at which the parameter values of the respective parameters visualized by the plots are considered uncritical for the patient's health condition, and to visualize a plot with overlap with another plot at times, at which the parameter values of the parameter of said plot are considered critical for the patient's health condition.

For outputting the generated time-dependent plots for visualization on the display 11 a data output 23 is provided, such as a data output interface coupled between the processor 22 and the display 11.

FIG. 3 shows several embodiments of timing diagrams illustrating time-dependent plots generated by a device or method according to the present invention illustrating various patient-related parameters over time (here over six days).

Figure 3A:
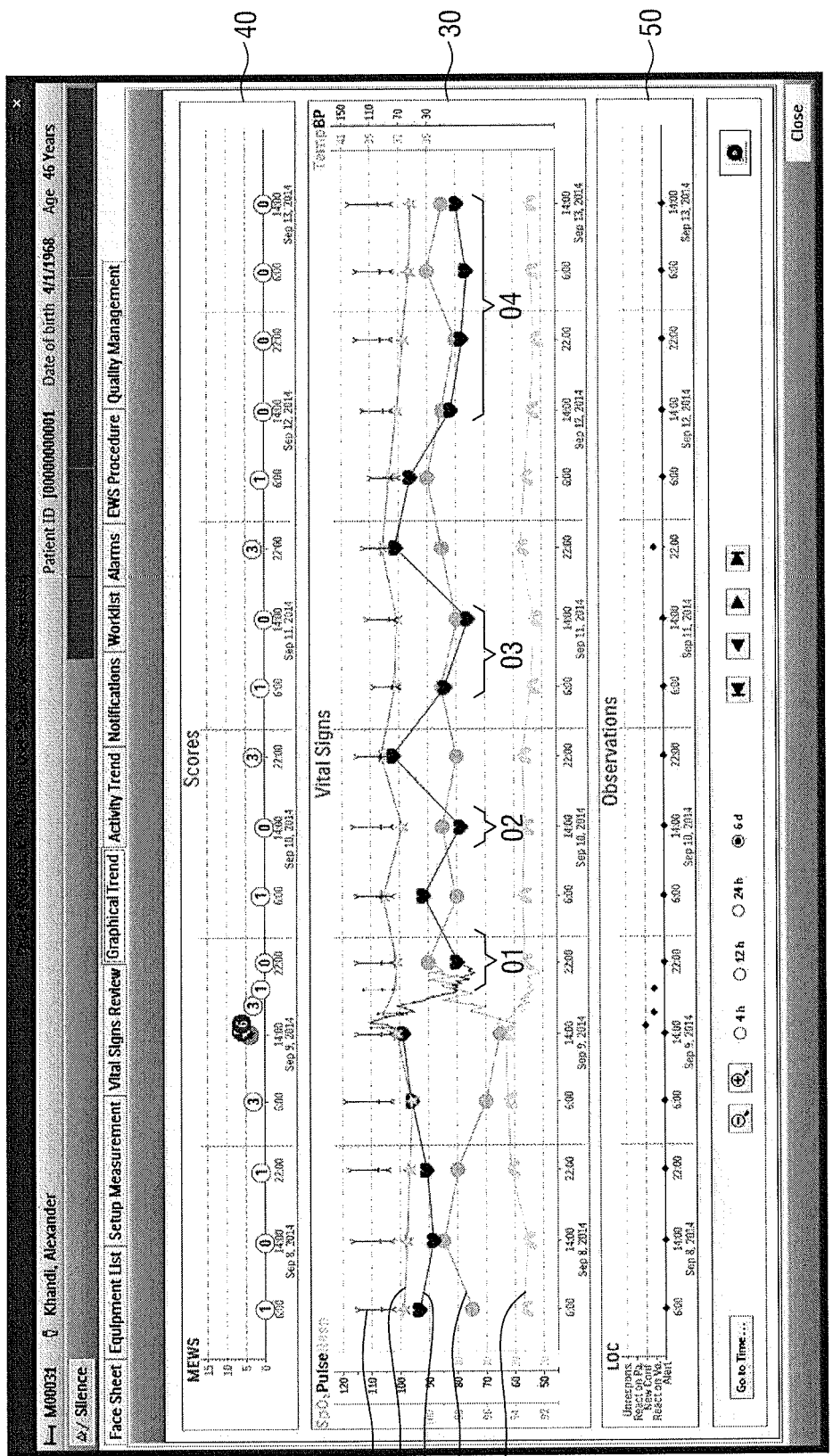
FIG. 3A shows an embodiment of a timing diagram in which several plots are visualized over time.

FIG. 3A shows a first embodiment of a timing diagram 30 in which several plots (also called trends) are visualized over time, including (from top to bottom) a plot 31 for blood pressure (BP) a plot 32 for temperature (Temp), a plot 33 for heart rate (Pulse), a plot 34 for blood oxygen saturation (SpO2) and a plot 35 for respiration rate (Resp). In this embodiment the plots 32 to 35 are visualized as lines connecting the available parameter values of the respective patient-related parameter. Further, the parameter values are separately indicated by different icons (e.g. dots for SpO2, hearts for HR). The plot 31 for blood pressure is indicated by range indications indicating the systolic, mean and diastolic pressure at the respective moment in time.

As can be seen in FIG. 3A the plots are generally arranged such that they do not overlap (i.e. cross each other) which shall be understood such that the respective parameters are in an uncritical range, i.e. the health condition of the patient is uncritical. The scale, baseline, position and range of the plots are selected accordingly. For instance, for the plot 35 for RR the scale, baseline, position and range are selected such that the plot 35 is the lowermost part in the timing diagram 30. Since the RR is normally in the range between 10 and 20, this range is located at the lowermost part of the timing diagram 30 and can not extend to upper regions of the timing diagram. For the neighboring plot 34 the SpO2 is normally in the range between 94% and 100%, which range is located accordingly so that the plot 34 does normally (i.e. for uncritical values of SpO2 and RR) not cross the plot 35. If the SpO2 dropped below approximately 93% or 94%, the plots 34 and 35 would cross (i.e. overlap) indicating a potentially critical health condition of the patient (because of a too low SpO2).

In FIG. 3A such overlaps O1, O2, O3, O4 can be seen from day 2 to day 6 between plot 33 for HR and plot 34 for SpO2. Said plots 33, 34 cross each other multiple times and thus overlap for longer time periods (i.e. whenever plot 34 is above plot 33), compared to the "normal" (uncritical) situation (e.g. on day 1) in which plot 33 is above plot 34. These overlaps O1, O2, O3, O4 between these plots 33, 34 thus clearly indicate in an easily recognizable way to a caregiver (e.g. by transmitting all plots or selected plots showing the overlap or a message to the caregiver's smartphone or computer) that the health condition of the patient is potentially critical so that the caregiver can check this and take immediate action if required. Further overlaps appear between the plot 31 for BP and plot 32 for temperature on days 2 to 5 and between plot 32 for temperature and plot 33 for HR on day 2.

As can be seen from the saw-tooth parts of plots 32-35 on day 2, a negative score 6 was issued (shown in the score diagram 40). Due to this negative score and/or due to the overlaps of the plots the measurement intervals were shortened, e.g. by the caregiver or automatically, i.e. the patient was monitored more carefully instead of the spot checks three times per day as done otherwise in this example. Thus more intensive measurement provides more measurement data resulting in the saw-toothed parts of the plots. During this time no icons (e.g. hearts or circles) are preferably used to indicate measurement points, but only lines are drawn. After the health state of the patient improved again, the measurement intervals were enlarged again to three measurements per day as on day 1.

In FIG. 3A further diagrams and further information is depicted including a score diagram 40 depicting the calculated MEWS (modified early warning score) over time and an observations diagram 50 depicting the LOC (level of consciousness) over time. Further, various general information (such as the patient's name, ID, birthday and age) and various buttons are shown for selecting or changing visualizations, settings or menu items.

Figure 3B:
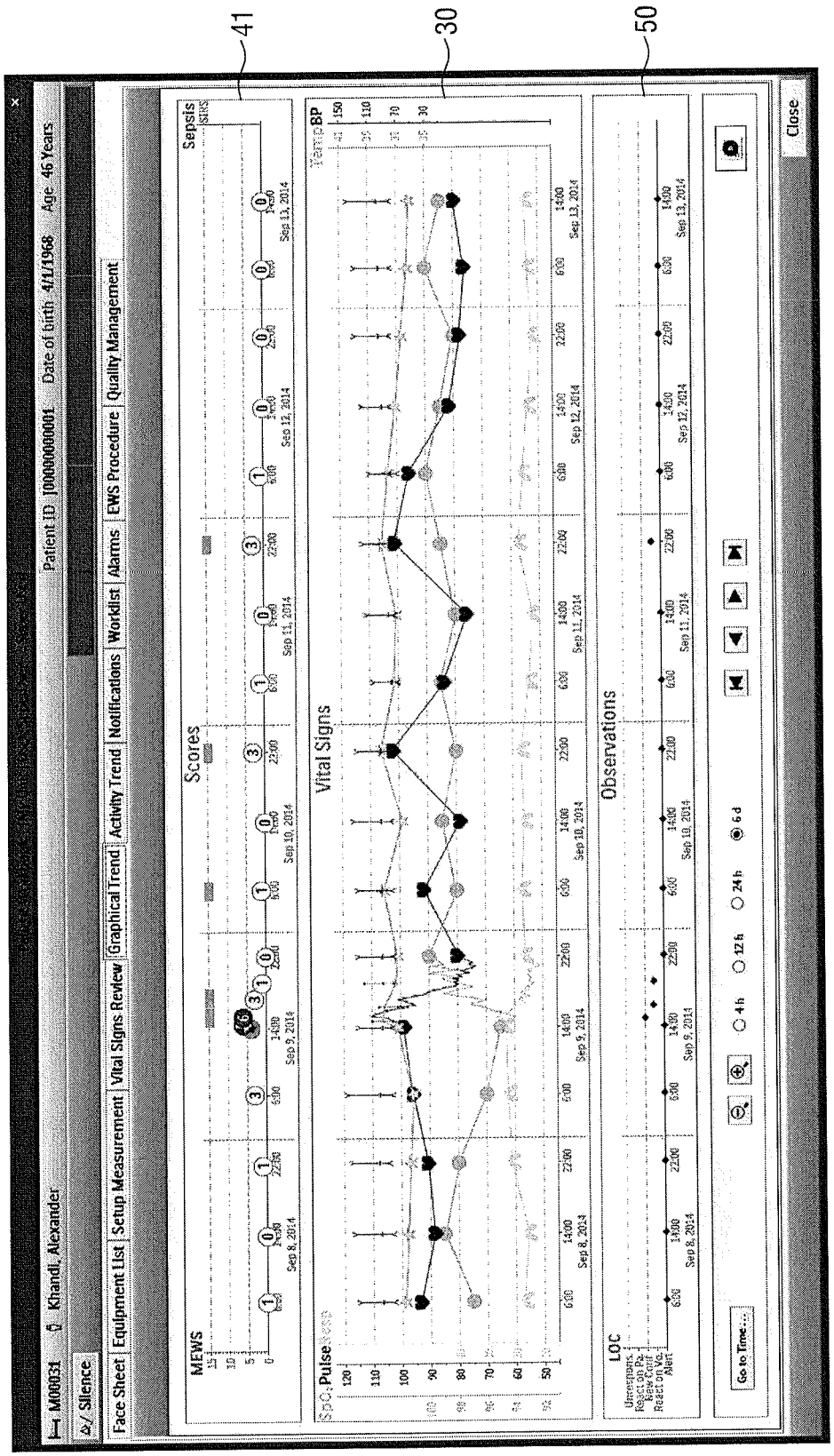
FIG. 3B shows an embodiment of a diagram in which several plots are visualized over time.

FIG. 3B shows a second embodiment of different diagrams. Compared to the diagrams shown in FIG. 3A the score diagram 41 is slightly different than the score diagram 40. The score diagram 41 indicates, in addition to the MEWS, sepsis, in particular if SIRS (systemic inflammatory response syndrome) is given (SIRS) at a certain moment (which is the case in this example on days 2, 3 and 4).

Figure 3C:
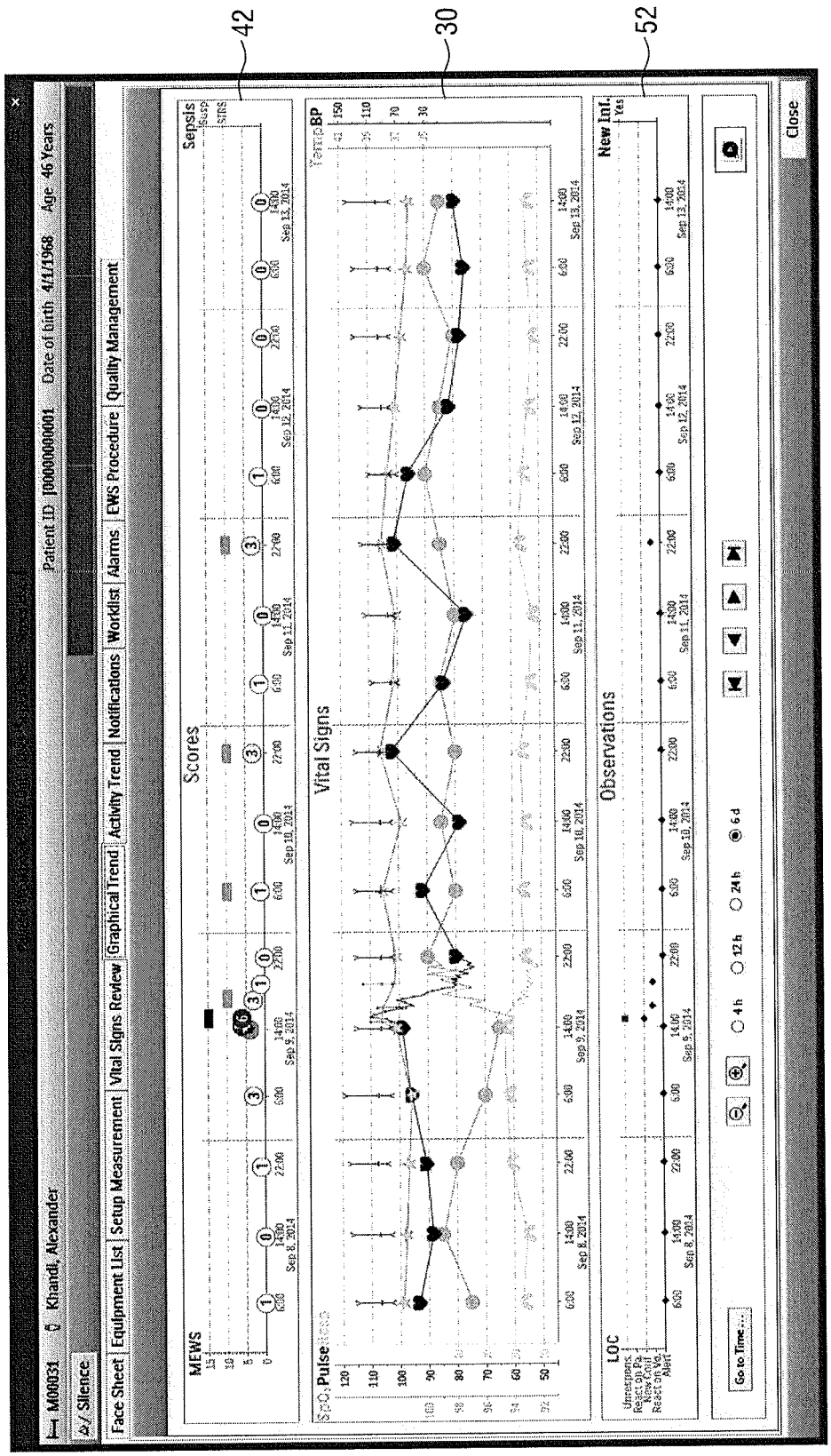
FIG. 3C shows an embodiment of a diagram in which several plots are visualized over time.

FIG. 3C shows a third embodiment of different diagrams. Compared to the diagrams shown in FIG. 3B the score diagram 42 is slightly different by not only indicating if SIRS is given but also if sepsis is suspected (Susp) (which is the case in this example on day 2). Further, the observations diagram 52 additionally indicates if a new infection (New Inf.) is detected (which is the case in this example on day 2), which easily allows recognizing if a caregiver should take a close look.

Figure 3D:
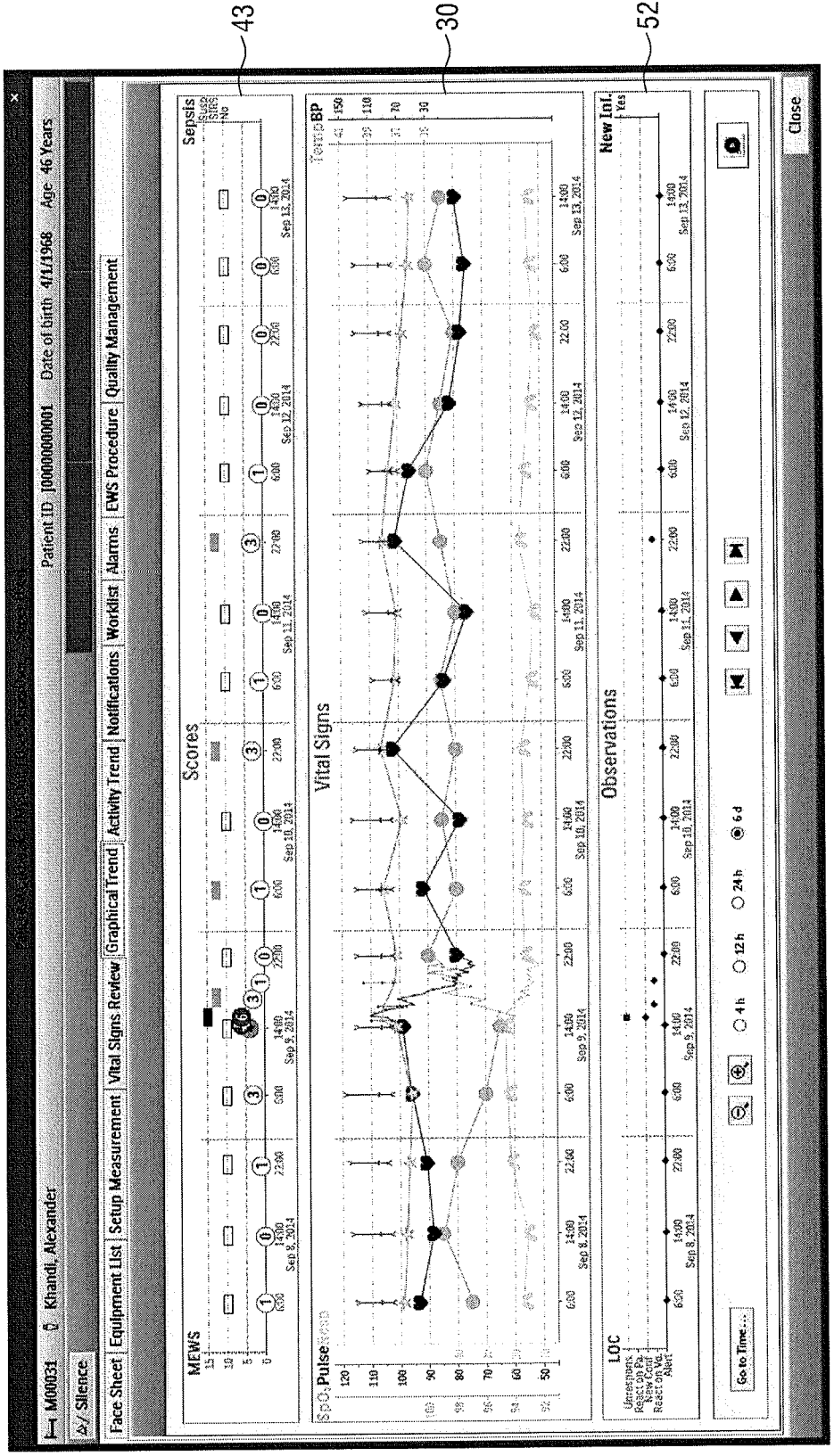
FIG. 3D shows an embodiment of a diagram in which several plots are visualized over time.

FIG. 3D shows a fourth embodiment of different diagrams. Compared to the diagrams shown in FIG. 3C the score diagram 43 is slightly different by additionally not only indicating if sepsis is suspected or SIRS is given, but also if sepsis is not given (No) (which is the case in this example on days 1, 5 and 6 and partly on days 2 to 4). Here, the advantage can be seen not to trend some limits with single parameters since in the normal case the graphical trend is not visually overloaded.

Figure 3E:
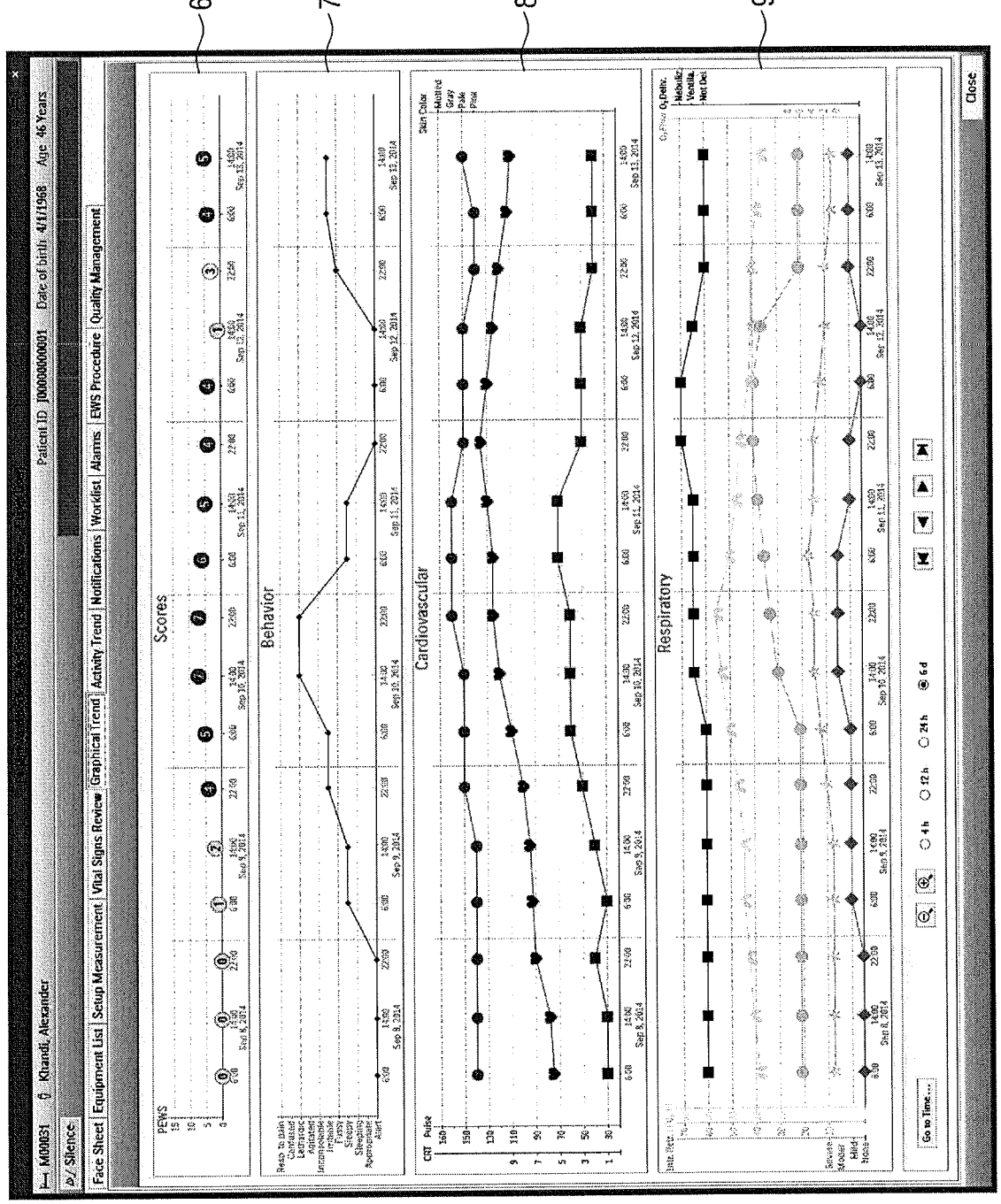
FIG. 3E shows an embodiment of a diagram in which several plots are visualized over time.

FIG. 3E shows a fifth embodiment of different diagrams. Said diagrams include a score diagram 60 indicating PEWS (pediatric early warning score), a behavior diagram 70 indicating the patient's behavior, a cardiovascular diagram 80 indicating different cardiovascular parameters in the form of plots and a respiratory diagram 90 indicating different respiratory parameters in the form of plots. The plots in the diagrams are hereby generally generated and visualized as described above for the present invention.

Figure 3F:
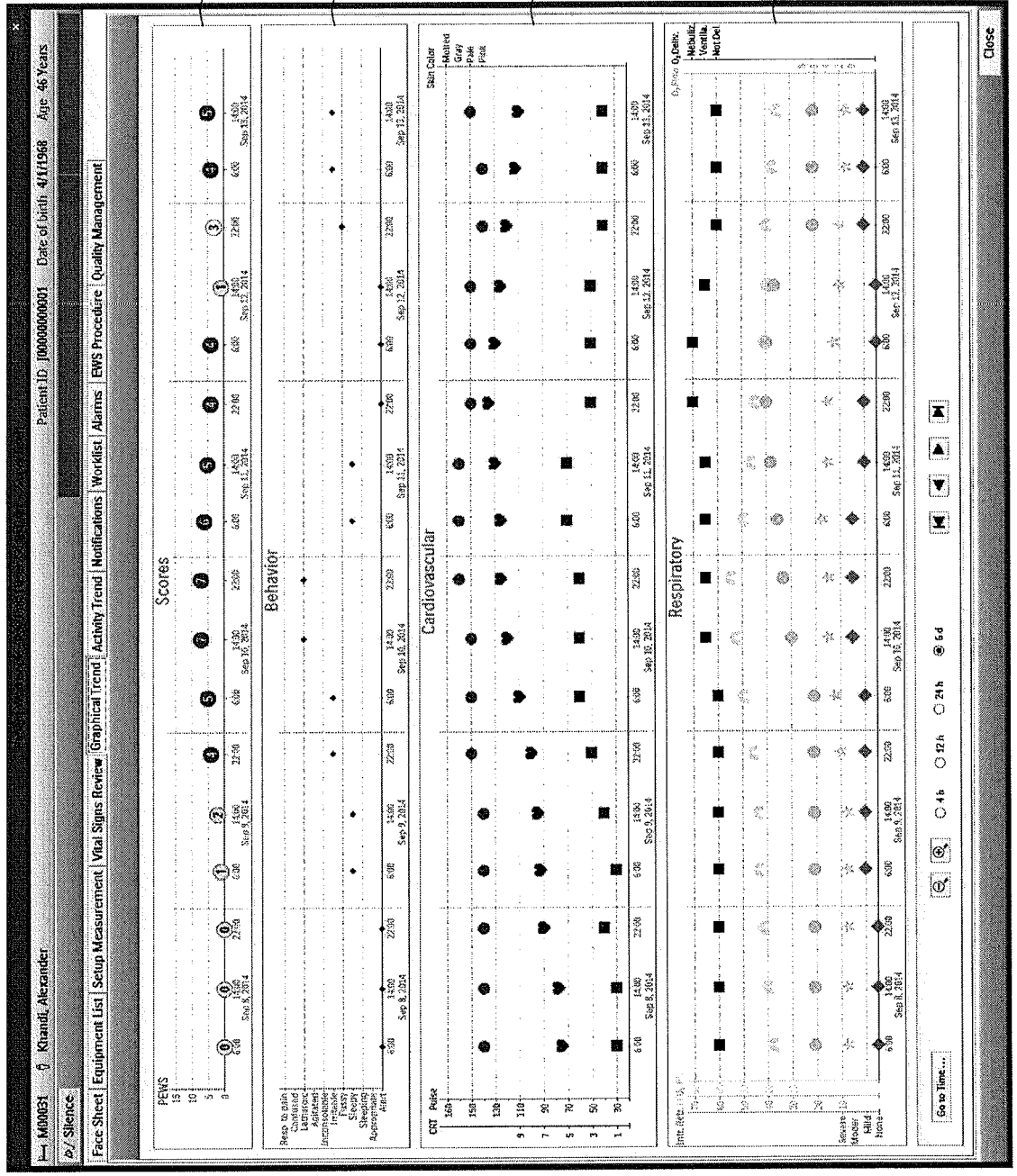
FIG. 3F shows an embodiment of a diagram in which several plots are visualized over time and parameter values are indicated as singular points.

FIG. 3F shows a sixth embodiment of different diagrams similar to FIG. 3E. However, in the diagrams 71, 81, 91 shown in FIG. 3F the plots are not visualized by lines as in FIG. 3E, but the parameter values are indicated as singular points.

Figure 3G:
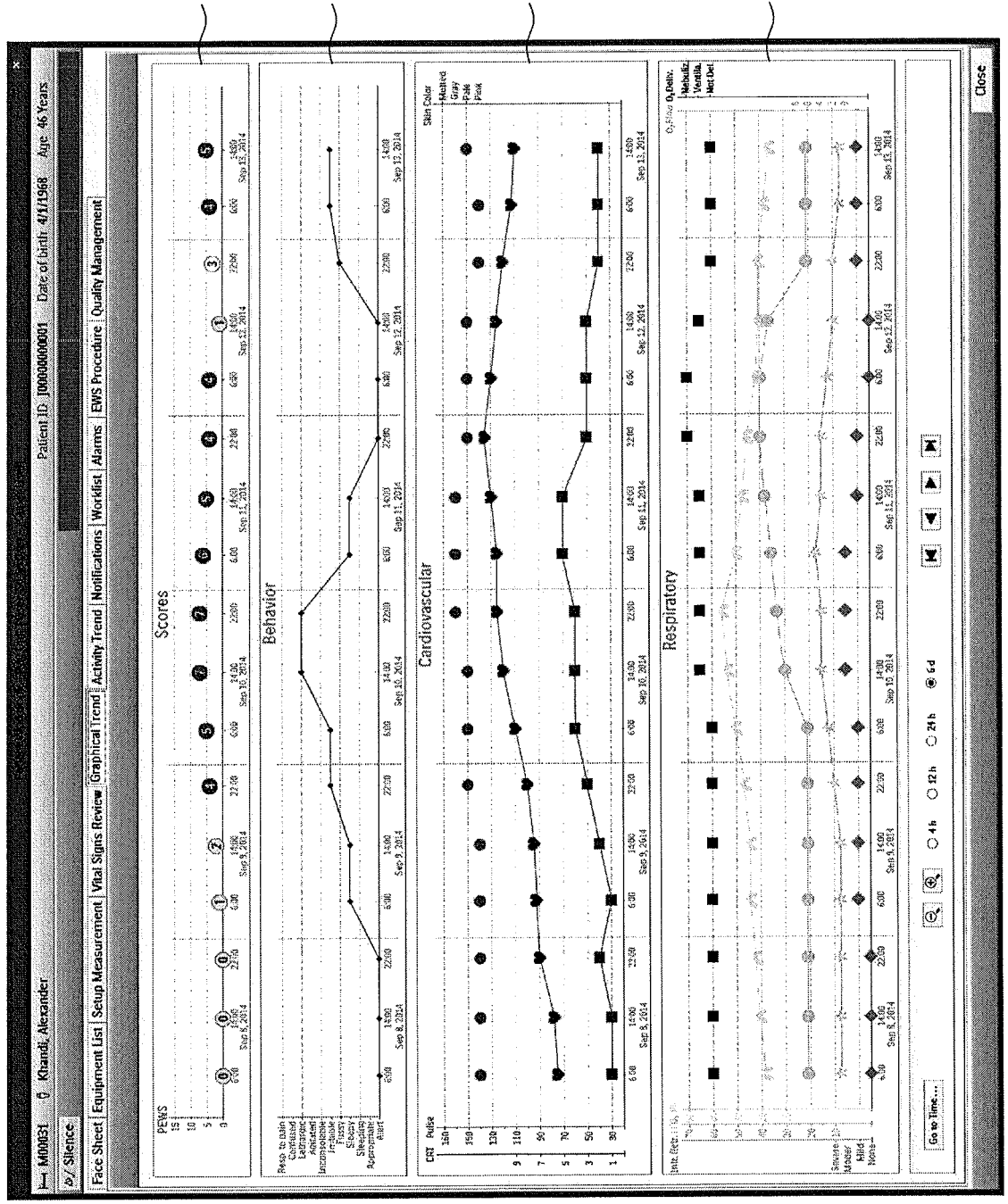
FIG. 3G shows an embodiment of a diagram in which several plots are visualized over time and some of the plots are visualized by lines and some are visualized by singular points.

FIG. 3G shows a seventh embodiment of different diagrams similar to FIGS. 3E and 3F. However, in the diagrams 82, 92 shown in FIG. 3G some of the plots are visualized by lines as in FIG. 3E, while for other plots (particularly those at which the parameter can only take on dedicated states or parameter values) only the parameter values are indicated as singular points.

Generally, the plots can be visualized in any possible form, i.e. in any color, font, line thickness, line style (dotted, broken, continuous, . . . ), etc. Further, in the diagrams shown in FIG. 3 the time axis is a horizontal axis, but may alternatively be a vertical axis. Still further, different symbols or icons may be used, such as circle, square, rhombus, heart, etc. The user may even add own icons, e.g. to adapt the visualization to the commonly used style, e.g. of the hospital.

Figure 3H:
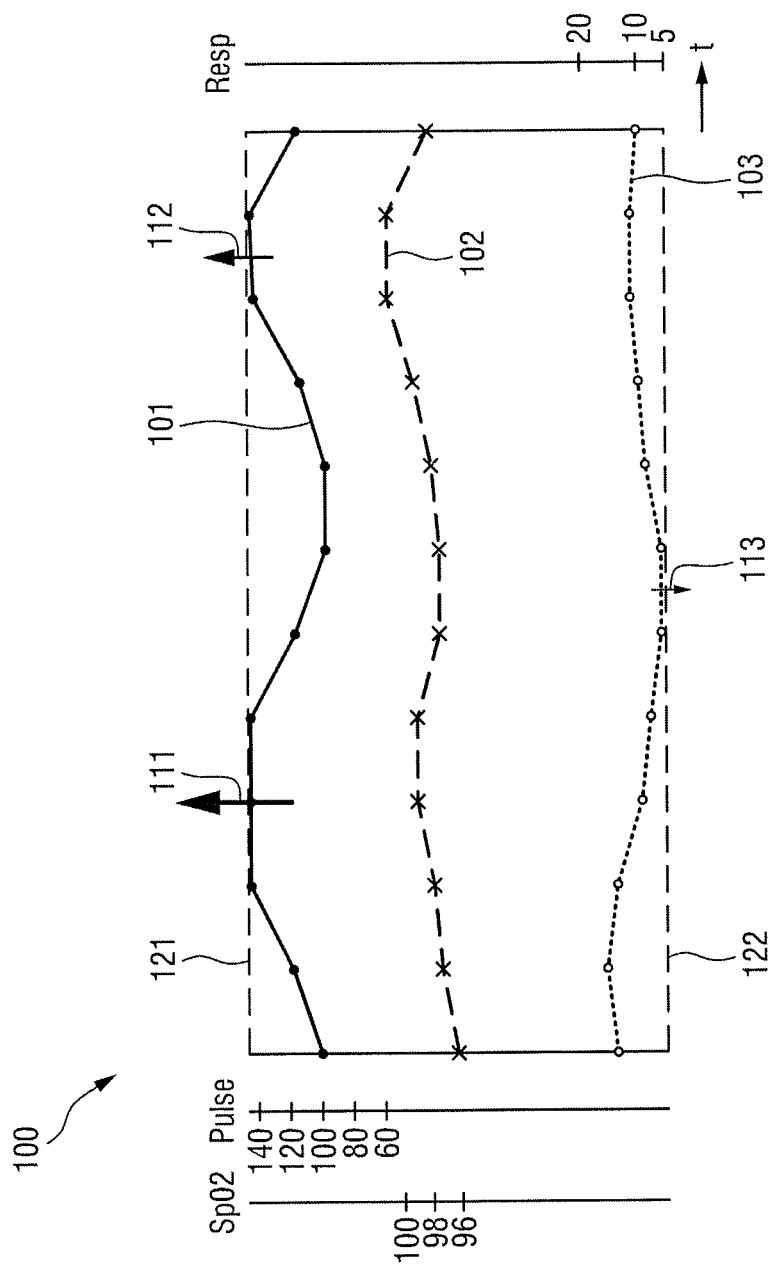
FIG. 3H show an embodiment of a simplified timing diagram showing three plots for three different patient-related parameters.

FIG. 3H shows an eighth embodiment of a simplified timing diagram 100 showing three plots for three different patient-related parameters including plot 101 for HR, plot 102 for SpO2 and plot 103 for RR over time t. Further, for the uppermost plot 101 overlap indicators 111, 112 are shown in FIG. 3H if the plot 101 exceeds (overlaps) an upper threshold indicator 121, i.e. since the uppermost plot 101 has no further plot above it, with which it could overlap, the upper threshold indicator 121 (here a horizontal line) is provided. An overlap with this upper threshold indicator 121 shall thus be understood as an indication that the parameter values of the parameter of the uppermost plot 101 increase to be considered critical for the patient's health condition, i.e. if the HR exceeds a value of 140 in this example.

Similarly, for the lowermost plot 103 an overlap indicator 113 is shown in FIG. 3H if the plot 103 falls below (overlaps) a lower threshold indicator 122, i.e. since the lowermost plot 103 has no further plot below it, with which it could overlap, the lower threshold indicator 122 (here a horizontal line) is provided. An overlap with this lower threshold indicator 122 shall thus be understood as an indication that the parameter values of the parameter of the lowermost plot 103 decrease to be considered critical for the patient's health condition, i.e. if the RR falls below a value of 5 in this example.

The overlap indicators 111, 112, 113 are generated in a way that they indicate to which extent the uppermost plot 101 overlaps with the upper threshold indicator 121 or the lowermost plot 103 overlaps with the lower threshold indicator 122. In other words, the user can directly recognize from the overlap indicator how strong the patient's health condition is potentially deteriorated.

In the example shown in FIG. 3H the overlap indicators 111, 112, 113 are visualized as arrows having different line thickness and length indicating the extent to which the respective threshold indicator is exceeded. For instance, the overlap indicator 111 is a longer arrow with a larger thickness than the overlap indicator 112, which indicates that the upper threshold indicator 121 is exceeded by the plot 111 at this time to larger extent (i.e. the HR value is higher) than at the time of the overlap indicator 112. The arrow as overlap indicator shall hereby be understood as an example only; many other kinds of indicators may be used as well, such as a number indicating the extent, a triangle of different size, etc.

Figure 3I:
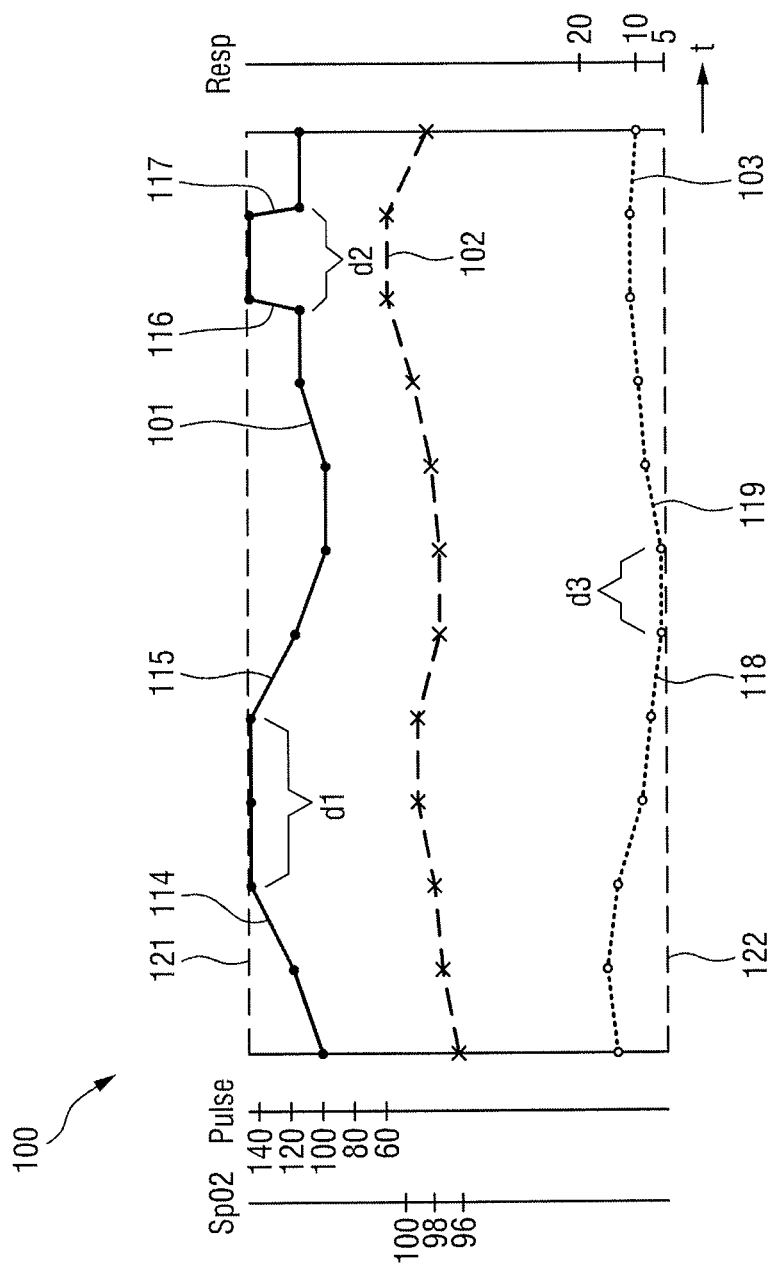
FIG. 3I shows an embodiment showing an inclination of portions of the plots.

In the example shown in FIG. 3I the inclination (gradient) of portions 114-119 of the respective plots just before and/or just after a plot reaches the upper or lower threshold indicator 121, 122, respectively, is interpreted as overlap indicator. For instance, the inclination of portions 118, 119 is smaller than the inclination of portions 116, 117, which is smaller than the inclination of portions 114, 115. The larger the inclination, the more exceeds the plot the respective threshold indicator 121, 122. In other words, the large inclination of portions 116, 117 indicates that the plot 101 much exceeds the upper threshold indicator 121 (i.e. HR reaches rather high values above 140), whereas the small inclination of portions 118, 119 indicates that the plot 103 falls below the lower threshold indicator 122 to a small extent only (i.e. the RR is only a little bit smaller than 5).

Additionally, the distance between the crossings of a plot with the respective threshold indicator may be used as (additional or alternative) indicator how serious the deterioration of the health condition may potentially be. For instance, a larger distance d1 may be used as indication of a more serious deterioration whereas a smaller distance d2, d3 may be used as indication of a less serious deterioration.

Still further, other indicators may be additionally used for indication of a potential deterioration of the patient's health condition. For instance, the color, line thickness or icons used for visualization of a plot may change if the respective parameter values become critical, or the plot may start blinking, or an additional sign (e.g. an exclamation mark) may be shown in addition to the plot where it starts to become critical. For instance, the portions 114, 116 and the portions where plot 101 reaches the upper threshold indicator may be visualized in a different color and/or line thickness (and/or may be blinking) than the rest of the plot 101 to indicate that the parameter values of the HR underlying the plot 101 have become critical.

The patient monitor may further comprise a user interface 12 as shown in FIG. 2. Said user interface 12, which may be a common interface or which may comprise several subinterfaces, may be configured to allow the user to perform one or more functions. In practical implementations the user interface 12 may comprise one or more of a touchpad, keypad, computer mouse, knob(s), switch(es), etc.

In particular, via the user interface 12 the user may be allowed to select and/or modify the scale, baseline, position, range and/or kind of visualization (e.g. with or without connecting lines between parameter values, the use of icons for the parameter values, etc.) of the plots. Further, via the user interface 12 the user may be allowed to select a point of a plot or a complete plot, wherein said display 11 is configured to display the parameter value of the parameter at the selected point of said plot or of all parameters at the moment in time of the selected point or the parameter values of the parameter of the complete selected plot. Still further, via the user interface 12 the user may be allowed to hide one or more plots by selecting a plot that shall not be hidden or by selecting plots that shall be hidden. This has the advantage that parameter values superposed (hidden) by other parameter values can be visualized and recognized in a better way.

In one embodiment general default values for the scale, baseline, position and range of the plots are used. Preferably, however, patient-related default values for selecting the scale, baseline, position and range of the plots are used, wherein said patient-related default values are selected based on one or more of age, size, weight, body mass index, gender, health status, current treatment, current medication, state of consciousness, and patient category of the patient. These default values may e.g. be stored in a look-up table or other storage for access by the device. In other embodiments the scale, baseline, position and range of the plots may be determined individually for the patient based on one or more of age, size, weight, body mass index, gender, health status, current treatment, current medication, state of consciousness, and patient category of the patient.

The proposed plots (also called graphical trends) are able to visualize multiple vital signs, scores and the overall patient condition. It allows the user (e.g. a caregiver, physician, hospital staff, etc.) to easily assess the patients' health condition and its development. The reason for deterioration of the overall score can be easily determined without user interaction. The visualization of multiple vital signs, events, alarms and lab results in a single graphical trend allows the hospital staff to easily assess how these data relate to each other. This creates a new innovative and easy way of forecasting the patient's health trend and therefore is able to be used as a trigger for hospital staff to counteract medical situations before they even happen.

Preferably, the proposed graphical trends are fully configurable in order to fit the clinical workflows and to support the hospital staff as best as possible. One or more of the following items are preferably configurable:
The amount of charts visualized at the same time as well as their size. Size can be configured to fit the available space or set to a fixed size.
Each chart can display multiple vital signs and other data.
Color, position, stroke size, icons, y-axis position (left or right).
Specific icons can be assigned to each individual parameter. Spike values can be assigned to different icons in order to easily detect them.
Additional icons can be imported.
Horizontal and vertical grid lines can be added.
A headline for each chart can be specified to name groups, e.g. body systems.
Each parameter can be assigned a description with or without the unit.
The parameter range can be adjusted.
Each parameter can be positioned within the chart by defining an offset. This allows the parameter to be visualized at any position within the chart without any scaling and overlapping effects.
The background color can be adjusted in order to fit the lighting conditions of the work environment.

The functionality of the proposed graphical trends is way beyond the normal functionality of a regular chart application. Deterioration of a patient" health condition is often influenced by multiple complex reasons. By combining all currently visible vital signs with additional data such as lab results, BMI, BSA, ADT data and other data the proposed graphical trend is able to trigger counteractions much earlier than currently existing chart applications in order to save lives.

Preferred features of the proposed graphical trend include:
By moving over or clicking a specific value more information is being displayed containing all available vital signs and other data which were valid at that time. This allows the user to identify which input data lead to a specific score.
A single parameter can be visualized in multiple charts at the same time.
Icons will be automatically replaced by dots to avoid overlapping.
Zooming and scrolling modifies the whole display area in order to preserve the context between the separate charts.
Y-axis value range can be adjusted by patient category, e.g. adult, neonatal, etc.
If display space is limited (e.g. on tablets) all vital signs can be displayed on top of each other.
For better overview each trended vital sign can be temporarily hidden within the graphical trend by clicking on its Y-axis.
Automatic time scrolling can be enabled to ensure the newest recorded vital signs and data are always visible.
Recorded vital signs and data which are located outside of the visible scale area will be hinted at by an icon at the top or bottom of the chart.

In summary, the present invention making use of a certain visualization of plots or graphical trends is a new and innovative way of connecting and visualizing several different vital parameters, lab data, ADT data and more in order to trigger hospital staff to counteract patient health deterioration. This allows the hospital staff, or generally any user such as a caregiver, to easily get a complete overview about a patient's health condition and its development.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

A computer program may be stored/distributed on a suitable non-transitory medium, such as an optical storage medium or a solid-state medium supplied together with or as part of other hardware, but may also be distributed in other forms, such as via the Internet or other wired or wireless telecommunication systems.

Any reference signs in the claims should not be construed as limiting the scope.

The invention claimed is:

1. A device for visualization of patient-related data, comprising:
   a data input for obtaining patient-related data of a patient over time,
   a processor for processing the obtained patient-related data for visualization by operations including:
   generating time-dependent plots of at least two different patient-related parameters over time derived from the obtained patient-related data, said plots being generated for common visualization in a common timing diagram having a common time axis on a display;
   selecting the scale, baseline, position and range of the plots to visualize (i) the plots in the common timing diagram without overlap at times, at which the parameter values of the respective parameters visualized by the plots are considered uncritical for the patient's health condition, and (ii) a given plot of said plots with overlap with another plot of said plots visualized in the common timing diagram at times, at which the parameter values of the parameter of said given plot are considered critical for the patient's health condition;
   changing, at each overlap point on the plots, the position of intersecting plots relative to each other from a position of the plots before the overlap occurred along the common timing diagram, and
   a data output for outputting the generated time-dependent plots for visualization on a display.

2. The device as claimed in claim 1,
wherein the processor is configured to use general default values for the scale, baseline, position and range of the plots.

3. The device as claimed in claim 1,
wherein the processor is configured to use patient-related default values for selecting the scale, baseline, position and range of the plots, said patient-related default values being selected based on one or more of age, size, weight, body mass index, gender, health status, current treatment, current medication, state of consciousness, patient category of the patient.

4. The device as claimed in claim 1,
wherein the processor is configured to determine the scale, baseline, position and range of the plots individually for the patient based on one or more of age, size, weight, body mass index, gender, health status, current treatment, current medication, state of consciousness, patient category of the patient.

5. The device as claimed in claim 1,
wherein the processor is configured to select the scale, baseline, position and range of the plots to be visualized in the common timing diagram as uppermost and lowermost plots such that the uppermost plot overlaps with an upper threshold indicator at times, at which the parameter values of the parameter of the uppermost plot increase to be considered critical for the patient's health condition, and the lowermost plot overlaps with a lower threshold indicator at times, at which the parameter values of the parameter of the lowermost plot decrease to be considered critical for the patient's health condition.

6. The device as claimed in claim 5,
wherein the processor is configured to generate an overlap indicator at the overlap of the uppermost plot with the upper threshold indicator and at the overlap of the lowermost plot with the lower threshold indicator.

7. The device as claimed in claim 6,
wherein the processor is configured to generate the overlap indicator in a way that it indicates to which extent the uppermost plot overlaps with the upper threshold indicator or the lowermost plot overlaps with the lower threshold indicator.

8. The device as claimed in claim 1,
wherein the processor is configured to select the scale, baseline, position and range of the plots dependent on the display type and/or size.

9. A patient monitor comprising:
   a device for visualization of patient-related data, comprising:
   a data input for obtaining patient-related data of a patient over time,
   a processor for processing the obtained patient-related data for visualization by operations including:
   generating time-dependent plots of at least two different patient-related parameters over time derived from the obtained patient-related data, said plots being generated for common visualization in a common timing diagram having a common time axis on a display;
   selecting a scale, baseline, position and range of the plots to visualize (i) the plots in the common timing diagram without overlap at times, at which the parameter values of the respective parameters visualized by the plots are considered uncritical for the patient's health condition, and (ii) a given plot of said plots with overlap with another plot of said plots visualized in the common timing diagram at times, at which the parameter values of the parameter of said given plot are considered critical for the patient's health condition; and
   changing, at each overlap point on the plots, the position of intersecting plots relative to each other from a position of the plots before the overlap occurred along the common timing diagram; and
   a data output for outputting the generated time-dependent plots for visualization on a display;
   and
   a display configured to visualize the time-dependent plots generated by said device.

10. The patient monitor as claimed in claim 9,
further comprising a user interface allowing a user to select and/or modify the scale, baseline, position, range and/or kind of visualization of the plots.

11. The patient monitor as claimed in claim 9,
further comprising a user interface allowing a user to select a point of a plot or a complete plot, wherein said display is configured to display the parameter value of the parameter at the selected point of said plot or of all parameters at the moment in time of the selected point or the parameter values of the parameter of the complete selected plot.

12. The patient monitor as claimed in claim 9,
further comprising a user interface allowing a user to hide one or more plots by selecting a plot that shall not be hidden or by selecting plots that shall be hidden.

13. A system for patient monitoring, comprising:
   a plurality of sensors for acquiring patient-related data and
   a patient monitor as claimed in claim 9 for obtaining and processing the acquired patient-related data.

14. A non-transitory computer readable medium storing instructions executable by a computer to perform a method for visualization of patient-related data, comprising:
obtaining patient-related data of a patient over time,
processing the obtained patient-related data for visualization by operations including:
generating time-dependent plots of at least two different patient-related parameters over time derived from the obtained patient-related data, each patient-related parameter having a defined normal range, said plots being generated for common visualization in a common timing diagram having a common time axis on a display,
selecting the scale, baseline, position and range of the plots to visualize the plots in the common timing diagram without overlap at times, at which the parameter values of the respective parameters visualized by the plots are inside their respective defined normal ranges, and (ii) a given plot of said plots with overlap with another plot of said plots visualized in the common timing diagram at times, at which the parameter values of the parameter of said given plot are outside its defined normal range,
changing, at that any overlap of the plots indicative of a potentially critical situation for the patient's health, the position of intersecting plots relative to each other from a position of the plots before the overlap occurred along the common timing diagram; and
outputting the generated time-dependent plots for visualization on a display.

15. The non-transitory computer readable medium as claimed in claim 14, wherein the method further includes:
using patient-related default values for selecting the scale, baseline, position and range of the plots, said patient-related default values being selected based on one or more of age, size, weight, body mass index, gender, health status, current treatment, current medication, state of consciousness, patient category of the patient.

16. The non-transitory computer readable medium as claimed in claim 14, wherein the method further includes:
determining the scale, baseline, position and range of the plots individually for the patient based on one or more of age, size, weight, body mass index, gender, health status, current treatment, current medication, state of consciousness, patient category of the patient.

17. The non-transitory computer readable medium as claimed in claim 14, wherein the method further includes:
selecting the scale, baseline, position and range of the plots to be visualized in the common timing diagram as uppermost and lowermost plots such that the uppermost plot overlaps with an upper threshold indicator at times, at which the parameter values of the parameter of the uppermost plot increase to be considered critical for the patient's health condition, and the lowermost plot overlaps with a lower threshold indicator at times, at which the parameter values of the parameter of the lowermost plot decrease to be considered critical for the patient's health condition.

18. The non-transitory computer readable medium as claimed in claim 17, wherein the method further includes:
generating an overlap indicator at the overlap of the uppermost plot with the upper threshold indicator and at the overlap of the lowermost plot with the lower threshold indicator.

19. The non-transitory computer readable medium as claimed in claim 18, wherein the method further includes:
generating the overlap indicator in a way that it indicates to which extent the uppermost plot overlaps with the upper threshold indicator or the lowermost plot overlaps with the lower threshold indicator.

20. The non-transitory computer readable medium as claimed in claim 14, wherein the method further includes:
selecting the scale, baseline, position and range of the plots dependent on the display type and/or size.

* * * * *